United States Patent [19]
Osborn

[11] Patent Number: 5,576,459
[45] Date of Patent: Nov. 19, 1996

[54] QUATERNARY NITROGEN OR PHOSPHORUS CHIRATES

[75] Inventor: Morey E. Osborn, Austin, Tex.

[73] Assignee: Sachem, Inc., Austin, Tex.

[21] Appl. No.: 471,843

[22] Filed: Jun. 6, 1995

Related U.S. Application Data

[63] Continuation of Ser. No. 190,633, Feb. 2, 1994, abandoned.

[51] Int. Cl.$^6$ ..................................................... C07C 59/08
[52] U.S. Cl. ..................... 562/589; 562/553; 562/585; 562/579; 562/602; 564/286; 564/290; 564/295
[58] Field of Search ..................................... 562/585, 589, 562/553, 579, 602; 564/295, 286, 290

[56] References Cited

U.S. PATENT DOCUMENTS

| | | | |
|---|---|---|---|
| 2,661,370 | 12/1953 | Barber | 260/501 |
| 2,812,350 | 11/1957 | Niederhauser | 260/501 |
| 2,933,529 | 4/1960 | Hwa | 260/567.6 |
| 3,142,685 | 7/1964 | Buckler et al. | 260/340.7 |
| 3,223,718 | 12/1965 | Scherr et al. | 260/404 |
| 3,325,523 | 6/1967 | Albert | 260/404 |
| 3,636,114 | 1/1972 | Tobler et al. | 260/567.6 |
| 3,769,346 | 10/1973 | Boissier et al. | 260/567.6 P |
| 3,819,656 | 6/1974 | Barie, Jr. et al. | 260/343.7 |
| 3,972,855 | 8/1976 | Martinsson et al. | 260/567.6 M |
| 4,205,183 | 5/1980 | Hong | 562/401 |
| 4,313,895 | 2/1982 | Richmond et al. | 260/501.15 |
| 4,320,063 | 3/1982 | Kaplan | 260/404.5 |
| 4,444,881 | 4/1984 | Urbas | 435/139 |
| 4,670,192 | 6/1987 | Tenud et al. | 260/501.15 |
| 4,692,543 | 9/1987 | Tenud et al. | 558/342 |
| 4,732,709 | 3/1988 | Tenud et al. | 260/501.15 |
| 4,892,944 | 1/1990 | Mori et al. | 544/107 |

Primary Examiner—Gary Geist
Assistant Examiner—Barbara S. Frazier
Attorney, Agent, or Firm—Renner, Otto, Boisselle & Sklar

[57] ABSTRACT

An optically-active or chiral compound is described which comprises (A) at least one quaternary nitrogen or phosphorus cation provided that if the cation is a quaternary nitrogen cation containing a hydroxyalkyl group, the hydroxyalkyl group is free of chlorine, and (B) at least one optically-active anion.

In one embodiment, the optically-active anion is an optically-active carboxylic acid anion. The process for preparing such optically-active compounds also is described and such compounds may be prepared by reacting (A) at least one quaternary nitrogen or phosphorus salt with (B) at least one optically-active reactant capable of reacting with the salt provided that if the salt is a quaternary nitrogen salt containing a hydroxyalkyl group, the hydroxyalkyl group is free of chlorine.

3 Claims, No Drawings

QUATERNARY NITROGEN OR PHOSPHORUS CHIRATES

This is a continuation of application Ser. No. 08/190,633 filed on Feb. 2, 1994, now abandoned.

TECHNICAL FIELD

This invention relates to optically-active or chiral quaternary nitrogen and quaternary phosphorus compounds. The invention also relates to a process for preparing such optically-active compounds.

BACKGROUND OF THE INVENTION

U.S. Pat. No. 4,892,944 (Mori et at) describes a process for producing quaternary ammonium salts and quaternary phosphonium salts by reacting a tertiary amine or phosphine with a carbonic acid diester to form the corresponding quaternary carbonate and thereafter mixing the carbonate with an acid resulting in decarboxylation. The quaternary salts are reported to be useful as catalysts for phase transfer reactions, electrolytes for aqueous and organic electrolytic solutions, various additives, medicaments, etc. The acids which may be utilized to form the quaternary salts may be inorganic acids such HF, HCl, $HNO_3$, $SO_4$, etc., or the acids may be organic acids such as 2-methyl-2-propyl pentanoic acid, acrylic acid, lactic acid; aliphatic polycarboxylic acids such as citric acid, malonic acid; aromatic carboxylic acids such as benzoic acid, toluic acid, etc.; aromatic polycarboxylic acids such as phthalic acid, etc.

Quaternary ammonium compounds are described in U.S. Pat. No. 3,972,855, and these compounds are described as being useful in the treatment of substrates such as plastic materials and textile materials to impart anti-static properties. In particular, the quaternary ammonium compounds described in the '855 patent contain a 2-hydroxy-oxy propylene group and an oxy alkylene group. The anion of the salt may be selected from the group consisting of chloride, bromide, iodide, nitrate, hydroxyl, phosphate, methyl sulfate, formate, acetate, propionate, citrate and tartrate.

U.S. Pat. No. 4,692,543 (Tenud et at) and U.S. Pat. No. 4,732,709 (Tenud et al) describe the preparation of optically-active di-(3-chloro-2-oxy-propyltrimethyl ammonium)-tartrate. The '709 patent is a divisional of the '543 patent. The two patents also describe a method for the production of optically-active carnitine nitric chloride from the optically-active tartrates. The process for the production of the optically-active tartrate comprises converting the racemic 3-chloro-2-oxypropyltrimethyl ammonium chloride by racemate resolution with L-(+)-tartaric acid in the presence of a trialkylamine into the di-[(−)-3-chloro-2-oxy-propyltrimethylammonium]-L-(+)-tartrate. Other processes for preparing the same optically-active tartrate are described in these patents.

SUMMARY OF THE INVENTION

An optically-active or chiral compound is described which comprises (A) at least one quaternary nitrogen or phosphorus cation provided that if the cation is a quaternary nitrogen cation containing a hydroxyalkyl group, the hydroxyalkyl group is free of chlorine, and (B) at least one optically-active an ion.

In one embodiment, the optically-active anion is an optically-active carboxylic acid anion. The process for preparing such optically-active compounds also is described and such compounds may be prepared by reacting (A) at least one quaternary nitrogen or phosphorus salt with (B) at least one optically-active reactant capable of reacting with the salt provided that if the salt is a quaternary nitrogen salt containing a hydroxyalkyl group, the hydroxyalkyl group is free of chlorine.

DESCRIPTION OF THE PREFERRED EMBODIMENTS

Optically-active or chiral compounds are described which comprise (A) at least one quaternary nitrogen or quaternary phosphorus cation provided that if the cation is a quaternary nitrogen cation containing a hydroxy alkyl group, the hydroxy alkyl group is free of chlorine, and (B) at least one optically-active anion.

In one embodiment the quaternary nitrogen cation and quaternary phosphorus cation may be represented by the formulae

or

wherein A is nitrogen or phosphorus, $R^1$, $R^2$, $R^3$ and $R^4$ are each independently alkyl groups, hydroxyalkyl groups which are free of chlorine when A is nitrogen, alkoxyalkyl groups, aryl groups or hydroxyaryl groups, or $R^1$ and $R^2$ together with A may form a heterocyclic group provided that if the heterocyclic group contains a C=A group, $R^3$ is the second bond, and $R^5$ is a divalent alkylene or arylene group.

When the groups $R^1$, $R^2$, $R^3$ and $R^4$ are alkyl groups, the alkyl groups generally will contain from 1 to about 20 carbon atoms and more often from about to about 10 carbon atoms. The alkyl groups $R^1$ thru $R^4$ may be linear or branched alkyl groups, and specific examples of such alkyl groups include methyl, ethyl, propyl, butyl, pentyl, hexyl, heptyl, octyl, isooctl, nonyl, decyl, isodecyl, dodecyl, tridecyl, isotridecyl, hexadecyl and octadecyl groups. Generally, when the $R^1$ thru $R^4$ groups are alkyl groups, the alkyl groups contain from 1 to 4 carbon atoms and may be methyl, ethyl, propyl, and butyl groups.

$R^1$, $R^2$, $R^3$ and $R^4$ also may be hydroxyalkyl groups containing from 1 to 20 carbon atoms and more often from 1 to about 10 carbon atoms, or alkoxyalkyl groups containing from 2 to about 20 carbon atoms, more often from about 2 to about 10 carbon atoms, aryl groups or hydroxyaryl groups. Examples of hydroxyalkyl groups include hydroxyethyl, the various isomers of hydroxypropyl, hydroxybutyl, hydroxypentyl, etc. Examples of alkoxyalkyl groups include methoxymethyl, methoxyethyl, methoxypropyl, ethoxymethyl, etc. Examples of various aryl and hydroxyaryl groups include phenyl, benzyl, and equivalent groups wherein benzene rings have been substituted with one or more hydroxy groups.

Any two of the groups $R^1$ thru $R^4$ may comprise alkylene groups joined together with the nitrogen or phosphorus atom to form a heterocyclic group containing two or more carbon atoms, preferably 2 to 6 carbon atoms, and more preferably from 4 to 5 carbon atoms, provided that if the heterocyclic group contains a C=N or a C=P bond, a third $R^1$ thru $R^4$ group is the second bond. Examples of such heterocyclic groups include aziridines and phosphiranes (2 carbon atoms) azetidines and phosphetanes (3 carbon atoms), pyrrolidines and phospholanes (4 carbon atoms), piperidines and phosphanes (5 carbon atoms).

The group $R^5$ in Formula II is a divalent alkylene or arylene group. The divalent alkylene groups may contain from 1 to about 20 or more carbon atoms, and the divalent arylene group may contain from 6 to 20 or more carbon atoms. Specific examples of divalent alkylene groups include methylene, ethylene, propylene, butylene, 2-methyl propylene, hexylene, octylene, etc. Examples of arylene groups include phenylene, o-xylylene, p-xylylene, etc.

Specific examples of the quaternary nitrogen cations represented by Formula I include tetramethylammonium, tetraethylammonium, tetrapropylammonium, tetrabutylammonium, tetra-n-octylammonium, trimethylethylammonium, dimethyldiethylammonium, trimethylhydroxyethylammonium, trimethylmethoxymethylammonium, trimethylethoxyethylammonium, dimethyldihydroxyethylammonium, methyltrihydroxyethylammonium, phenyltrimethylammonium, phenyltriethylammonium, benzyltrimethylammonium, benzyltriethylammonium, dimethylpyrolidinium, dimethylpiperidinium, diisopropylimidazolinium, N-alkylpyridinium.

Specific examples are quaternary phosphorus cations represented by Formula I wherein A is a phosphorus atom include: tetramethylphosphonium, tetraethylphosphonium, tetrapropylphosphonium, tetrabutylphosphonium, tetra-n-octylphosphonium, trimethylethylphosphonium, dimethyldiethylphosphonium, trimethylhydroxyethylphosphonium, trimethylmethoxymethylphosphonium, trimethylethoxyethylphosphonium, dimethyldihydroxyethylphosphonium, methyltrihydroxyethylphosphonium, phenyltrimethylphosphonium, phenyltriethylphosphonium, benzyltrimethylphosphonium and benzyltriethylphosphonium.

Specific examples of quaternary nitrogen cations represented by Formula II include N,N,N,N',N',N'-hexamethylmethylenediammonium; N,N,N,N',N',N'-hexabutyl-1,4-butylenediammonium; N,N,N,N',N',N'-hexabutyl-1,6-hexamethylenediammonium; N,N,N,N',N',N'-hexabutyl-1,4-phenylenediammonium; etc. Examples of phosphorus cations representative of Formula II include N,N,N,N',N',N'-hexamethyl-1,6-hexamethylenediphosphonium, etc.

The optically-active compounds wherein the cation is represented by Formulae I and II are generally represented by Formulae VII and VIII

or

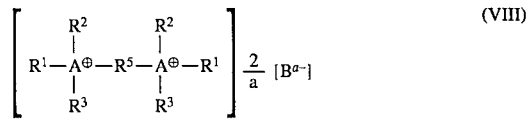

wherein A, $R^1$, $R^2$, $R^3$, $R^4$ and $R^5$ are as defined above with respect to Formulae I and II, $B^{a-}$ is at least one optically-active anion, and a is an integer equal to the total number of negative charges in the at least one anion.

The optically-active anion ($B^{a-}$) present in the optically-active compounds of Formulae VII and VIII may be selected from a variety of optically-active anions including oxy anions and carboxylic anions. The optically-active oxy anions may be represented by the general formula

and the optically-active carboxylic anions may be represented by the formula

wherein $R^{108}$ is an optically-active alkyl, cycloalkyl, aryl, arylalkyl, alkaryl or heterocyclic group containing at least one optically-active carbon atom. The alkyl groups may contain from 2 to 20 or more carbon atoms, and may be substituted or unsubstituted, and they may contain one or more heteratoms such as oxygen, sulfur, nitrogen, phosphorus, etc. Specific examples include —OH and —$NH_2$ substituents. The cycloalkyl groups may contain from 4 to 20 or more carbon atoms, and the aryl, alkaryl and arylalkyl groups may contain from 7 to 20 carbon atoms.

A wide variety of optically-active hydroxy compounds representative of Formula III are available for deriving useful oxy anions including the compounds listed below to illustrate Formula IIIA. Other optically-active hydroxy-containing compounds of Formula III include the D and L forms of: menthol; bi-2-naphthol; 2,2-dimethyl-1,3-dioxolane-4-methanol; phenylephrine; etc.

In one embodiment the optically-active oxy anions may be further represented by the formula

wherein $R^6$ is an alkyl, aryl or arylalkyl group, X is a group which is different from the three other groups attached to the same carbon atom, $R^6$ and X may be joined to form a cyclic group, and n is an integer of from 0 to 10. As noted earlier the alkyl, aryl and arylalkyl groups may contain one or more hetero atoms such as an O or N. In one embodiment, X in Formula IIIA is a group selected from R, OH, OR, $NH_2$ or a halide where R is an alkyl or aryl group.

Examples of optically-active oxy anions represented by the formula Formula IIIA include the anions derived from D- and L-forms of: 2-amino-1-propanol (alaninol); 2-butanol; 2-amino- 1-butanol; 2-amino- 1-pentanol; 4-methyl-1-hexanol; 2-octanol; 3-bromo-2-methyl- 1-propanol; 2-methoxy-1-butanol; 2-chloro- 1-butanol; 1,3-butanediol; arabinose; arabitol; fructose; galactose; 2-methoxy-2-phenylethanol; 1-phenyl-1-butanol; 1-phenyl-2-butanol; cis-4-hydroxyproline; α-phenylethyl alcohol; α-methylbenzyl alcohol; etc.

The optically-active carboxy anions may generally be represented by the formula $R^*COO^-$ (IV) wherein $R^*$ is may be an aliphatic, aromatic, cycloaliphatic or heterocyclic group, and these groups may be substituted with groups such as alkyl, OH, $NH_2$, COOH, etc. Examples of cyclic and heterocyclic optically-active carboxylic anions include anions derived from the D and L forms of: camphoric acid; camphorcarboxylic acid; menthoxyacetic acid; camphoracetic acid; campholic acid; proline; 4-hydroxyproline; thiazolidine-4-carboxylic acid; etc.

In another embodiment the optically-active carboxy anions may be represented by the formulae

or

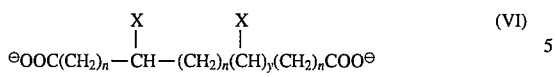
(VI)

wherein $R^6$ is an alkyl, aryl or arylalkyl group, X is a group which is different from the three other groups attached to the same carbon atom, $R^6$ and X may be joined to form a cyclic group, each n is independently an integer of from 0 to 10 and y is an integer of from 0 to 4. Although X' in Formulae V and VI may be any group which is different from the other three groups attached to the same carbon atom, X is generally selected from the group consisting of R, OH, OR, $NH_2$ or a halide group (where R is an alkyl or aryl group). In one embodiment, R is an alkyl group containing from about 1 to about 10 carbon atoms. As can be observed from the above formulae, the optically-active carboxylic anion may be a monocarboxylic anion (Formula V) or a dicarboxylic anion (Formula VI).

In another embodiment, the optically-active carboxylic anion may be represented by the formula

(VA)

wherein X is selected from the group consisting of R, OH, OR, $NH_2$ or a halide group wherein R is an alkyl group containing from 1 to about 10 carbon atoms and n is an integer of from 0 to about 10. Alternatively, the optically-active compound may be a dicarboxylic acid anion represented by the formula

(VIA)

wherein X is selected from the group consisting of R, OH, OR, $NH_2$ or a halide group wherein R is an alkyl group containing from 1 to about 10 carbon atoms.

Examples of optically-active carboxylic acid anions represented by Formula V wherein X is $NH_2$ include the anions derived from the following acids: D-alanine; L-alanine; D-2-amino-butyric acid; L-2-amino-butyric acid; (D) phenylalanine; L-phenylalanine; D-2-amino-1-pentanoic acid (Norvaline); L-2-2-amino-1-pentanoic acid; L-methionine; D-methionine; D-2-amino-4-pentanoic acid; and L-2-amino-4-pentanoic acid. Examples of optically-active anions of Formula V where X is OH include D-lactic acid, L-lactic acid. Examples of Formula V where $R^6$ is aryl and X is alkyl include D-2-hydroxy-1-butyric acid; and L-2-hydroxy-1-butyric acid; D-or-methyl benzoic acid; L-2-methyl benzoic acid; etc. Examples of Formula V wherein X is a halide include D-2-chloro-1-propionic acid; L-2-chloro-1-propionic acid; etc.

Examples of optically-active dicarboxylic acid anions such as those represented by Formula VI include the anions derived from D-maleic acid; L-maleic acid; D-tartaric acid; L-tartaric acid; D-aspartic acid; L-aspartic acid; D-dibenzoyl tartaric acid; L-dibenzoyl tartaric acid; di-para-toluoyl-D-tartrate; di-para-toluoyl-L-tartaric acid; D-2-aminoadipic acid; L-2-aminoadipic acid; D-camphoric acid; L-camphoric acid; etc.

Any of the above-described cations represented by Formulae I and II may be combined with any of the anions described above and represented by any one of the general Formulae III; IIIA; IV; IVA; V; VA; VI and VIA to form optically-active compounds as represented by Formula VII and VIII

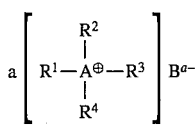
(VII)

or

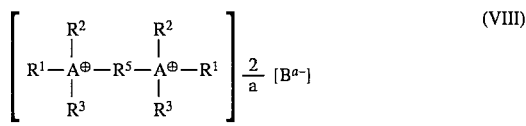
(VIII)

wherein A is a nitrogen or phosphorus atom, $R^1$, $R^2$, $R^3$ and $R^4$ are each independently alkyl groups containing from 1 to about 20 carbon atoms, hydroxyalkyl groups containing from 2 to about 20 carbon atoms and free of halogen when A is a nitrogen group, alkoxyalkyl groups containing from 2 to about 20 carbon atoms, aryl groups, or hydroxyaryl groups, or $R^1$ and $R^2$ together with A may form a heterocyclic group provided that if the heterocyclic group contains a C=A group, $R^3$ is the second bond, $R^5$ is a divalent alkylene or arylene group, a is an integer equal to the total number of negative charges in the at least one anion, and $B^{a-}$ is at least one optically-active anion.

The optically-active compounds of the present invention are neutral compounds. That is, the number of positive charges in the at least one cation is equal to the number of negative charges in the at least one anion. For example, when the cation contains one positive charge, and the anion contains one negative charge (that is, a in Formula VII is 1), the optically-active compound contains one cationic group and one anionic group (1 mole of each). Such types of optically-active salts are referred to herein as "QUAT CHIRATES," and specific examples of such optically-active compounds include: tetramethylammonium-D-lactate; tetraethylammonium-L-lactate; tetrabutylammonium-D-lactate; tetrabutylammonium-L-alanine; etc.

When the optically-active compound represented by Formula VII contains a cation containing one positive charge and an anion containing two negative charges such as, for example, the tartram and malate anions (that is a=2) the optically-active compound will contain two of the cation groups and one of the anion groups. Such types of optically-active compounds are referred to herein as "DIQUAT BIS-CHIRATES," and specific examples include di-tetramethylammonium-L-malate; di-tetramethylammonium-D-malate; di-tetrabutylammonium-L-tartrate; di-tetrabutylammonium-L-tartrate; di-tetrabutylphosphonium-D-tartrate; etc.

When the anion present in the optically-active compound represented by Formula VIII contains one negative charge (that is, a=1), two anions are required to neutralize the cation. Such types of optically-active compounds are referred to herein as "BISQUAT DICHIRATES" and specific examples of such optically-active compounds include N,N,N,N',N'-hexabutyl-1,6-hexamethylenediammonium-di-D-lactate,N,N, N',N',N'-hexabutyl- 1,6-hexamethylenediammonium-di-L-alanine; etc.

The optically-active compounds represented by Formula VIII which comprises a cation group containing two positive charges is combined with one anion group when the anion group contains two negative charges (i.e., a=2). Such types of optically-active compounds are referred to herein as "BISQUAT BISCHIRATES," and a specific example of such a compound is N,N,N,N',N',N'-hexabutyl,1,6-hexamethylenediammonium-L-tartrate. Examples of such optically-active compounds include N,N,N,N',N',N'-hexabutyl-1,6-hexamethylenediammonium-L-tartrate; N,N,N,N',N', N'-hexamethyl- 1,6-hexamethylenediammonium D malate; etc.

The four types of chirates may be illustrated as follows:

(1) QUAT CHIRATE

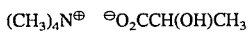
(CH$_3$)$_4$N$^\oplus$  $^\ominus$O$_2$CCH(OH)CH$_3$ (2) DIQUAT BISCHIRATE

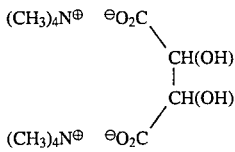

(3) BISQUAT DICHIRATE

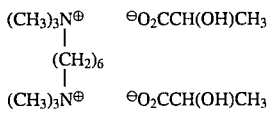

(4) BISQUAT BISCHIRATE

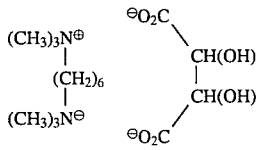

The optically-active compounds of the present invention may be prepared by a variety of reactions, and in general, may be prepared by reacting (A) at least one quaternary nitrogen or phosphorus salt with (B) at least one optically-active reactant capable of reacting with the salt. In general, the reaction comprises an anion exchange reaction of the quaternary ammonium salt such as a hydroxide, halide, carbonate, etc., which may be illustrated by the following equation

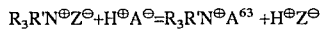

wherein A$^\oplus$ is an anion being exchanged and which may be any of the anions described above. In the above exchange reaction, Z may be any anion capable of reacting with the optically-active compound, and examples of such anions include OH$^-$ $^{HSO}$$_4$, HPO$_4$, halide, etc. When preparing optically-active quaternary ammonium salts by the above reaction, it is generally preferred that Z is a hydroxyl anion whereby the by-product formed is water thus resulting in the formation of optically-active salts of improved purity. For example, when Z is a halide, the by-product is an inorganic acid HZ which is more difficult to remove.

In one embodiment, the anion (A$^\ominus$) being exchanged may be an oxy anion derived from an alcohol such as R*OH wherein R* is as defined earlier, or a carboxy anion such as R*COO$^-$ derived from free acid R*COOH or an alkali metal salt of the free acid.

In one preferred embodiment, the optically-active compounds of the present invention may be prepared by reacting (A) at least one quaternary nitrogen or phosphorus salt represented by the formula

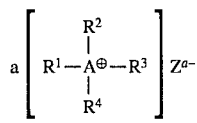

or

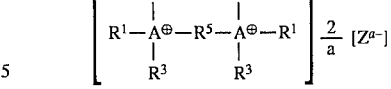

wherein A is a nitrogen or phosphorus atom, R$^1$, R$^2$, R$^3$ and R$^4$ are each independently alkyl groups, hydroxyalkyl groups which are free of halogen when A is a nitrogen group, alkoxyalkyl groups, aryl groups, or hydroxyaryl groups, or R$^1$ and R$^2$ together with A may form a heterocyclic group provided that if the heterocyclic group contains a C=A group, R$^3$ is the second bond, R$^5$ is a divalent alkylene or arylene group, a is an integer equal to the total number of negative charges in the at least one anion, and Z$^{a-}$ is at least one anion capable of reacting with an optically-active compound, with (B) at least one optically-active carboxylic acid or salt thereof represented by the formulae

R*COOY                    (IVA)

or

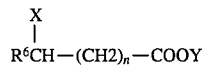

or

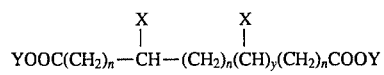

wherein R* is as defined in Formula IV, R$^6$ is an alkyl, aryl or arylallcyl group, X is a group which is different from the three other groups attached to the same carbon atom, R$^6$ and X in Formula VB and the two X groups in Formula VIB may be joined together to form a cyclic group, each n is independently an integer of from 0 to 10, y is an integer of from 0 to 4 and Y is a group capable of reacting with the quaternary salt.

In more specific embodiments, the anion Z$^{63}$ may be selected from the group consisting of OH, HSO$_4$, HPO$_4$, halide and CO$_3$, and in another embodiment, Y in Formulae IVA, VB and VIB is hydrogen or an alkali metal, and preferably, hydrogen. The X groups in Formulae IVA, VB and VIB may be R, OH, OR, NH$_2$, halogen or COOR wherein R is an alkyl or an aryl group. In general, the definitions of R$^1$ thru R$^5$ and A in Formulae IA and IIA are the same as the definitions in Formula I and II given previously, and similarly, the definition of the groups R$^6$, X, n and y in Formulae VB and VIB are the same as the definitions in Formulae V and VI.

The procedure for preparing the optically-active salts of the present invention generally involves reaction of the quaternary ammonium or quaternary phosphonium salt with an optically-active reactant such as a carboxylic acid, preferably in an aqueous solution at temperatures of from about ambient temperature to about 80° C. or 90° C. The optically-active reactant may be an alcohol when the reaction is conducted in an aprotic or non-aqueous solvent. The reaction is generally completed in a few hours but the reaction mixture is heated for an additional period to insure completion of the reaction. At the end of the reaction, the pH of the reaction mixture is adjusted to about 9–11 by the addition of either reactant as appropriate. The product is recovered and dried. Purities of at least about 90%, and even as high as 98% or more can be achieved.

The amounts of the quaternary salts and the optically-active compound used in the reaction are dependent on the number of charges in the quaternary salts and the number of reactive sites in the optically-active compound. Approximately equivalent amounts of the reactants are used in order to obtain an essentially neutral product; i.e., the number of ⊕ charges is equal the number of ⊖ charges. For the purpose of this invention, a quaternary ammonium or phosphonium salt or cation containing one positive charge contains one equivalent per mole. A di-quaternary ammonium or di-phosphonium salt or cation containing two positive charges contains two equivalents per mole. Similarly, anions containing one negative charge contain one equivalent per mole, and anions containing two negative charges contain two equivalents per mole.

The following examples illustrate the preparation of the optically-active quaternary compounds of the present invention. Unless otherwise indicated in the following examples and elsewhere in the specification and claims, all parts and percentages are by weight, temperatures are in degrees centigrade, and pressures are at or near atmospheric pressure.

EXAMPLE 1

To one kilogram of a stirred aqueous solution containing 35% of tetraethylammonium hydroxide (2.38 moles, 2.38 equivalents) at ambient temperature is added 214.4 grams (2.38 moles, 2.38 equivalents) of crystalline L-lactic acid (melting point 53° C.). The resulting mixture is stirred at an elevated temperature of about 50°–80° C. and maintained at this temperature overnight to insure completion of the reaction. The pH of the reaction mixture is adjusted to about 10.5 with either the tetramethylammonium hydroxide or the L-lactic acid as needed. The crude reaction mixture is dried by means of a rotary vacuum or tray vacuum drier until the product is 98+% pure by total dissolve solids (TDS) or acid fitration assay. The resulting product recovered is tetraethylammonium-L-lactate, a QUAT CHIRATE.

EXAMPLE 2

To one kilogram of a stirred aqueous solution containing 20% by weight of tetrabutylphosphonium hydroxide ("TBPH") (0.72 mole, 0.72 equivalent) at ambient temperature is added 141.3 grams (0.72 mole, 0.72 equivalent) of crystalline D-camphorcarboxylic acid (melting point 127° C.). The resulting mixture is stirred at a temperature of from about 40° C. to about 70° C. and maintained at this temperature overnight to insure completion of the reaction. The pH of the mixture is adjusted to approximately 10.0 with either TBPH or camphorcarboxylic acid as appropriate. The crude reaction mixture is dried by means of a rotary vacuum or tray vacuum drier until the product is 98+% pure by TDS or acid fitration assay. The resulting product recovered is tetrabutylphosphonium-D-camphorcarboxylate, a QUAT CHIRATE.

EXAMPLE 3

To 500 grams of a stirred aqueous solution containing 15% by weight of N,N,N,N',N',N'-hexabutyl-1,6-hexamethylenediammonium dihydroxide (0.165 mole, 0.33 equivalent) at ambient temperature is added 29.7 grams (0.33 mole, 0.33 equivalent) of crystalline D-lactic acid (melting point 127° C.). The resulting mixture is stirred at a temperature of from 30° C. to about 60° C., and the mixture is maintained at this temperature overnight to insure complete reaction. The pH of the reaction mixture is adjusted to about 9.5 and is then dried by means of a rotary vacuum drier until the product is 98+ pure by TDS or acid titration assay. The product which is recovered is N,N,N,N',N',N'-hexabutyl-1,6-hexamethylenediammonium-di-D-lactate, a BISQUAT DICHIRATE.

EXAMPLE 4

The procedure of Example 3 is repeated except that only 24.7 grams (0.165 mole, 0.33 equivalent) of L-tartaric acid is used. The reaction mixture is heated at a temperature of about 30° to about 60° C. for about 24 hours. The pH of the reaction mixture is adjusted to about 10, and the product is dried. Approximately 95 grams of N,N,N,N',N',N'-hexabutyl- 1,6-hexamethylene-diammonium-L-tartrate, a BISQUAT BISCHIRATE, is obtained.

EXAMPLE 5

To one kilogram of a stirred aqueous solution containing 2.12 moles ((2.12 equivalents) of tetrabutylammonium hydroxide (TBH) at ambient temperature there is added 142.14 grams (1.06 moles, 2.12 equivalents) of L-malic acid in a manner similar to Example 1. After heating the mixture overnight, the pH of the mixture is adjusted to 10.5 and dried under vacuum. The product obtained in this manner is di-tetrabutylammonium-L-malate monohydrate, a DIQUAT BISCHIRATE.

The optically-active compounds of the present invention which comprise at least one quaternary nitrogen cation or phosphorus cation and at least one optically-active anion may be used in a variety of applications. For example, the optically-active compound are useful as phase transfer catalysts, if chiral induction is desired, or as an electrolyte for aqueous or organic electrolytic solutions, or for imparting antistatic properties to substrates such as fabrics. The optically-active compounds also may be useful in optically-active cavity formation in zeolite manufacture under certain conditions; in polymerization to alter tacticity or strength properties; in in vitro applications such as precision drug delivery; in optically-active product mixture resolution; and in drug modeling.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

I claim:

1. An optically-active compound comprising (A) at least one quaternary nitrogen cation represented by the formula

wherein $R^1$, $R^2$ and $R^3$ are each independently alkyl groups, hydroxyalkyl groups which are free of chlorine, alkoxyalkyl groups, aryl groups, hydroxyaryl groups, or $R^1$ and $R^2$ together with N may form a heterocyclic group provided that if the heterocyclic group contains a C=N group, $R^3$ is the second bond, and $R^5$ is a divalent alkylene or arylene group; and (B) at least one optically-active anion, represented by the formulae $$R^6CH-(CH_2)_n-COO^\ominus \quad\text{(V)}$$

or $$^\ominus OOC(CH_2)_n-CH-(CH_2)_n(CH)_y(CH_2)_nCOO^\ominus \quad\text{(VI)}$$

(with X substituents on the CH groups)

wherein $R^6$ is an alkyl, aryl, or arylalkyl group, X is selected from the group consisting of R, OH, OR, $NH_2$ or a halide group wherein R is an alkyl or aryl group, $R^6$ and X in Formula V and the two X groups in Formula VI may be joined to form a cyclic group, each n is independently an integer of from 0 to 10 and y is an integer of from 0 to 4 provided the anion (VI) is not a tartrate anion.

2. An optically-active compound comprising (A) at least one quaternary nitrogen cation represented by the formula $$R^1-\overset{R^2}{\underset{R^3}{N^\oplus}}-R^5-\overset{R^2}{\underset{R^3}{N^\oplus}}-R^1 \quad\text{(II)}$$

wherein $R^1$, $R^2$ and $R^3$ are each independently alkyl groups, hydroxyalkyl groups which are free of chlorine, alkoxyalkyl groups, aryl groups, hydroxyaryl groups, or $R^1$ and $R^2$ together with N may form a heterocyclic group provided that if the heterocyclic group contains a C=N group, $R^3$ is the second bond, and $R^5$ is a divalent alkylene or arylene group; and (B) at least one optically-active anion represented by the formula $$R^6CH-(CH_2)_n-COO^\ominus \quad\text{(V)}$$

(with X substituent on the CH)

wherein $R^6$ is an alkyl, aryl, or arylalkyl group, X is selected from the group consisting of R, OH, OR, $NH_2$ or a halide group wherein R is an alkyl or aryl group, $R^6$ and X in Formula V may be joined to form a cyclic group and each n is independently an integer of from 0 to about 10.

3. An optically-active compound comprising:

(A) at least one quaternary nitrogen cation represented by the formula $$R^1-\overset{R^2}{\underset{R^3}{N^\oplus}}-R^5-\overset{R^2}{\underset{R^3}{N^\oplus}}-R^1 \quad\text{(II)}$$

wherein $R^1$, $R^2$ and $R^3$ are each independently alkyl groups or aryl groups, and $R^5$ is a divalent alkylene or arylene group; and (B) at least one optically-active lactate ion.

* * * * *